United States Patent [19]

Liepins

[11] Patent Number: 5,223,269
[45] Date of Patent: Jun. 29, 1993

[54] METHODS AND COMPOSITION FOR THE TREATMENT OF HYPERTENSION

[76] Inventor: Andrejs Liepins, 331 Hamilton Avenue, St. John's, Newfoundland, Canada, A1B 3V6

[21] Appl. No.: 700,616

[22] Filed: May 15, 1991

Related U.S. Application Data

[63] Continuation-in-part of Ser. No. 402,059, Aug. 31, 1989, abandoned.

[51] Int. Cl.$^5$ .............................................. A61K 33/00
[52] U.S. Cl. .................................................... 424/600
[58] Field of Search ........................................ 424/600

[56] References Cited

U.S. PATENT DOCUMENTS

| | | | |
|---|---|---|---|
| 4,002,663 | 1/1977 | Miyano | 560/121 |
| 4,259,523 | 3/1981 | Bollinger | 562/500 |

OTHER PUBLICATIONS

CA 99(25):212409j, Wyrick et al., 1983.
CA 112(13):111824x, Vasdev et al., 1990.

Primary Examiner—Frederick E. Waddell
Assistant Examiner—Kimberly R. Jordan
Attorney, Agent, or Firm—Dressler, Goldsmith, Shore, Sutker & Milnamow, Ltd.

[57] ABSTRACT

Methods and compositions of a deuterium-containing compound are disclosed that are utilized in the treatment of hypertension. Compositions containing deuterium oxide, deuterated foods or deuterated antihypertensive drugs dissolved or dispersed in a physiologically tolerable diluent are administered to patients in need of treatment for hypertensive disorders. Methods for the lowering of elevated blood pressure and for decreasing the likelihood of the onset of hypertension in a patient are disclosed.

10 Claims, 2 Drawing Sheets 5,223,269

METHODS AND COMPOSITION FOR THE TREATMENT OF HYPERTENSION

CROSS-REFERENCE TO RELATED APPLICATION

This application is a continuation-in-part of co-pending U.S. Ser. No. 07/402,059 filed on August 31, 1989, now abandoned.

TECHNICAL FIELD

The present invention relates to a method for the treatment of hypertension, and to a composition suitable for use in such treatment.

BACKGROUND OF THE INVENTION

Hypertension refers to a disorder that is characterized by an elevation of the systolic and/or diastolic blood pressure. This disorder is commonly classified as either primary (or essential) hypertension or secondary hypertension.

The etiology of primary hypertension is unknown and it is unlikely that there is a single causative basis for this disorder. There is strong evidence of a hereditary predisposition for hypertension as well as for the involvement of environmental factors such as dietary sodium intake, obesity and stress.

Secondary hypertension is usually associated with renal disease or such disorders as Cushing's syndrome, pheochromocytoma and hyperthyroidism. Secondary hypertension may also be associated with the use of oral contraceptives or excessive ingestion of alcohol.

In hypertension, there is either an increase in the total peripheral vascular resistance such as is due to vasoconstriction, or an increase in cardiac output, or both. These conditions produce an elevation in blood pressure because blood pressure is equal to flow times resistance. Increases in cardiac output and peripheral vascular resistance are commonly related to changes in either the sympathetic nervous system or the renin-angiotensin-aldosterone system mediated by the kidneys, lung and adrenal cortex.

In humans, an untreated hypertensive patient is at great risk of developing disabling or fatal left ventricular failure, myocardial infarction, cerebral hemorrhage or renal failure. Hypertension in humans is an important risk factor in predisposition to stroke and coronary atherosclerosis.

There is presently no cure for primary hypertension; however, drug therapy can usually modify its course. Such drug therapy commonly employs the administration of an oral diuretic (such as a thiazide derivative, a loop diuretic or metalazone) or a beta-blocker (such as propranolol and timolol or a cardioselective beta-blocker such as metoprolol, atenolol or acetbutolol). If these agents do not effectively control the hypertension, a sympathetic depressant and/or a vasodilator could be added. The administration of these agents requires close supervision of the patient and is characterized by frequent side effects.

The present invention is directed to a treatment and composition effective in reducing the elevated blood pressure associated with hypertension without reliance upon the aforementioned medications.

SUMMARY OF THE INVENTION

A method and a composition for the treatment of hypertension in a patient are contemplated by the present invention. Elevated blood pressure associated with hypertension in a patient is reduced by administering to the patient a therapeutically effective amount of a composition containing a physiologically tolerable deuterated compound, i.e., an amount sufficient to elevate the deuterium concentration in the patient's body fluids by at least about 300 percent. The composition is administered for a time period sufficient to effect a decrease of the patient's blood pressure. The deuterium-containing composition is preferably administered perorally; however, other modes of administration, e.g., intravenous, can be utilized as well. In a preferred embodiment, the composition contains at least about 10 weight percent of deuterium, calculated as deuterium oxide or heavy water.

The administration of the composition to a patient, at relatively low doses, can be continued so as to maintain a reduction of an elevated blood pressure and a reduction of the patient's systolic blood pressure as well.

Another aspect of the present invention contemplates a method for reducing the likelihood of the onset of hypertension in a patient that is at risk for the development of hypertension. This particular method contemplates the chronic administration of a therapeutically effective maintenance dose of a composition containing deuterium to a patient for a sustained period of time. It is contemplated that a maintenance dosage of the composition supplies about 125 milligrams (mg) to about 1700 mg of deuterium per kilogram (kg) of body weight per day to a patient. In a preferred embodiment, the composition contains about 10 to about 30 weight percent of deuterium, calculated as deuterium oxide, and is administered perorally.

A composition contemplated by the present invention contains a deuterium-containing compound together with a physiologically tolerable diluent. The deuterium-containing compound is contemplated to be a physiologically compatible, metabolizable deuterated compound and includes deuterium oxide, intravenous solutions that contain deuterium oxide, foods that contain deuterated carbohydrates or proteins, anti-hypertensive pharmaceutical compounds that have been deuterated, tricyclic antidepressants containing deuterium, and the like.

In a preferred embodiment, this composition is water or a saline solution that contain about 10 to about 90 weight percent of deuterium oxide, more preferably about 10 to about 30 weight percent of deuterium oxide, based on the weight of water. The amount of deuterium oxide administered by the composition is sufficient to provide a therapeutically effective antihypertensive effect when administered to a mammal at risk for blood pressure elevation in an appropriate dose.

BRIEF DESCRIPTION OF THE FIGURES

In the drawings forming a portion of this invention.

DESCRIPTION OF PREFERRED EMBODIMENT

Figure 1:
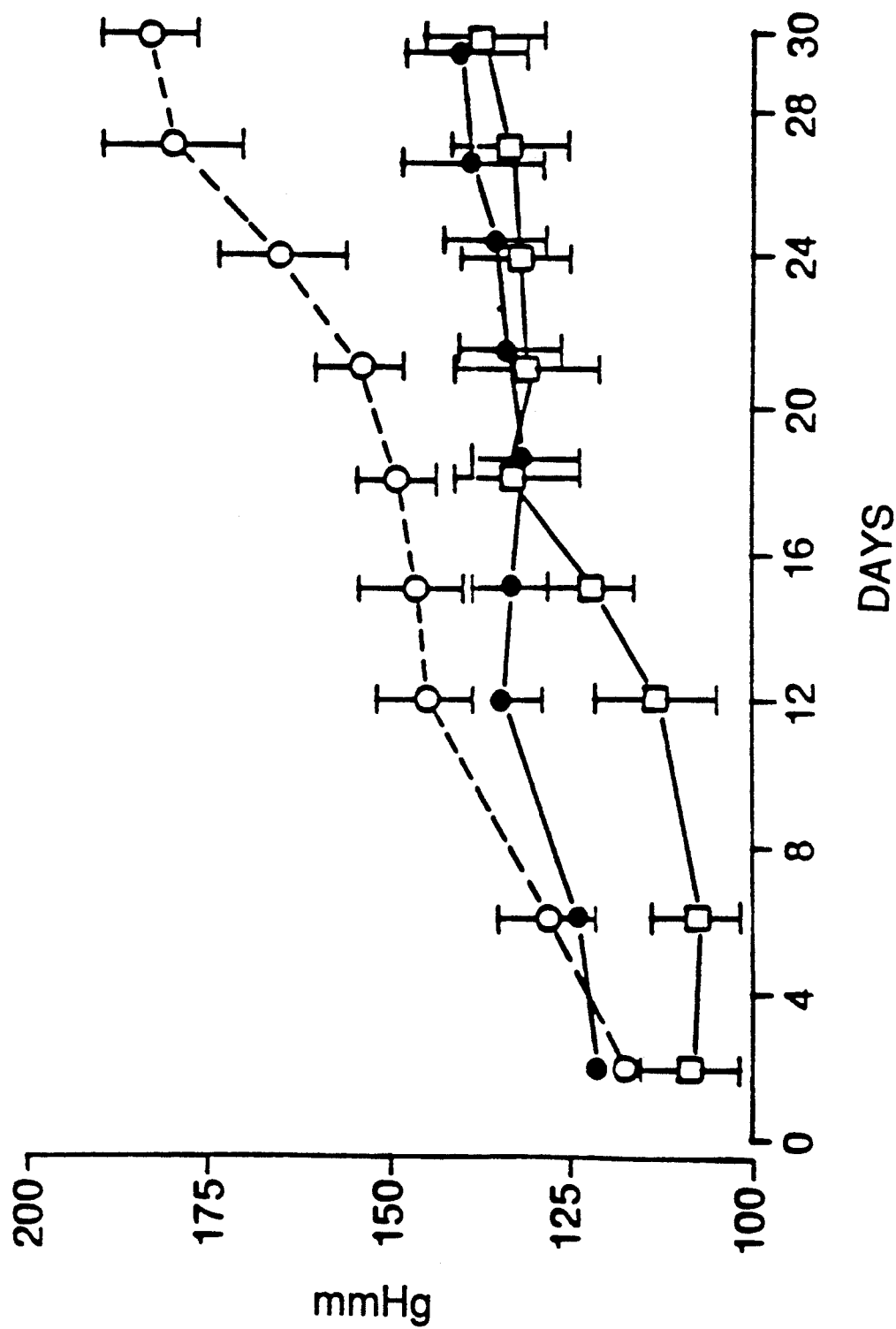
FIG. 1 is a graph depicting systolic blood pressure (SBP) in both young spontaneously hypertensive rats (SHR) and normotensive Wistar-Kyoto rats (WKY). Beginning at four weeks of age, the SHRs (three per group) received ad libitum either standard drinking water (O———O) or drinking water containing 25 percent by weight deuterium oxide (●———●). The control WKY rats received standard drinking water (□—□) during the same time period.

The present invention in its several aspects utilizes a deuterium-containing compound as the active ingredient to increase the deuterium level in a patient's body fluid.

Deuterium, or heavy hydrogen, is a stable, non-radioactive isotope of hydrogen and has an atomic weight of 2.0144. It is represented by the symbol D or $^2H$ and usually exists in the diatomic state. It is a colorless, odorless gas in nature. Deuterium can replace hydrogen in many molecules to produce deuterated compounds. Deuterium oxide ($D_2O$), also referred to as heavy water, is a preferred deuterium-containing compound and is composed of two atoms of deuterium bonded to one atom of oxygen. The mass difference between hydrogen and deuterium is the largest for any pair of stable, non-radioactive isotopes in the periodic table, and this difference accounts for many significant chemical and physical differences in the properties of $H_2O$ and $D_2O$, such as melting point (0 degrees C. for $H_2O$; 3.81 degrees C. for $D_2O$), boiling point (100 degrees C. for $H_2O$; 101.42 degrees C. for $D_2O$), density at 25 degrees C. (0.99701 g/cm$^3$ for $H_2O$; 1.1044 g/cm$^3$ for $D_2O$) and viscosity at 55 degrees C. (0.8903 millipascal second (mPa·S) for $H_2O$; 1.107 mPa·S for $D_2O$). Deuterium oxide is a distinctly more structured liquid than is ordinary water, and it is more extensively hydrogen-bonded. Deuterium oxide can be used to grow deuterated organisms such as molds, bacteria, algae, plankton and eukaryotic cells which are then capable of producing deuterated compounds or compositions of biological or physiological importance.

As used herein, the term "blood pressure" describes the pressure exerted by the blood upon the walls of the blood vessels, especially the arteries, that is usually expressed in millimeters of mercury (mm Hg) as a fraction having as numerator the maximum pressure that follows systole of the left ventricle of the heart (systolic blood pressure) and as denominator the minimum pressure that accompanies cardiac diastole (diastolic blood pressure). Normal blood pressure levels in humans vary with age, averaging from about 100/55 (systolic/diastolic) at birth to about 120/80 in a young adult to about 160/100 at about age 80.

As used herein, the term "hypertension" describes a condition in which an abnormally high arterial blood pressure is present; in a young adult, a hypertensive state is present usually when the diastolic blood pressure is greater than 90 mm Hg and the systolic blood pressure is greater than about 135 to 140 mm Hg.

As used herein, the term "physiologically tolerable diluent" refers to molecular entities and compositions that do not produce an allergic or similar untoward reaction such as gastric upset, dizziness and the like when administered to a patient and which are compatible with the deuterium compounds of the present invention and not deleterious to the recipient patient. Illustrative physiologically tolerable diluents include water ($H_2O$), emulsions with edible oils such as cottonseed oil, sesame oil, coconut oil, peanut oil and the like, elixirs and solutions such as isotonic saline and glucose solutions and the like.

As used herein, the term "equilibrium deuteration" describes the administration to a patient for a sustained time period of a sufficient dosage of a deuterated compound to produce a constant systemic level of deuterium in the patient.

As used herein, the term "deuterated compound" describes a compound in which one or more hydrogen atoms contained therein have been replaced with deuterium atoms. Deuterated compounds are produced either by chemical reaction with deuterium-containing reagents or biologically by growing organisms such as bacteria and molds in a deuterium oxide-containing medium.

The term "therapeutically effective amount" encompasses those amounts which provide antihypertensive activity without attendant adverse side effects. The precise amount to be utilized with a particular patient depends upon numerous factors such as method of administration, condition of the patient, the specific deuterated composition that is being administered, and the like.

Compositions contemplated by the present invention include deuterium oxide-enriched water, the so-called "heavy water" distributed as the discontinuous phase in a physiologically tolerable liquid medium, deuterium oxide-saline solutions, deuterated foods, deuterated antihypertensive pharmaceutical preparations, deuterated antidepressant preparations and the like, dissolved or dispersed in a physiologically tolerable diluent.

Deuterated foods include carbohydrates, such as sugars and starches, and proteins, polypeptides, as well as amino acids, e.g., L-tryptophan, and the like, that are deuterium-enriched. Such foods contain physiologically compatible, metabolizable deuterated compounds produced either synthetically or by the growth of natural organisms such as plants, molds, bacteria, algae, plankton, and the like, in deuterium-enriched water. Specific illustrative deuterated foods are fruit, e.g., apples, oranges, and the like, and vegetables, e.g., potatoes, carrots, beets, and the like.

Deuterated antihypertensive pharmaceutical preparations include antihypertensive drugs such as calcium channel blockers and diuretics that have been deuterium-substituted. Deuterium substitution in these compounds can potentiate their antihypertensive effects in a patient. Illustrative antihypertensive drugs are deuterated verapamil, deuterated propranolol and deuterated metalazone. Such compounds can be prepared by isotope exchange from verapamil, propranolol and metalazone, respectively.

Deuterium oxide-saline solutions embodying the present invention can be used to treat patients with essential hypertension who develop hypertensive crises during which blood pressures in excess of 160/100 (systolic/diastolic) may be reached under stressful conditions so as to reduce the likelihood of a cerebrovascular hemorrhage (stroke). Normal physiological saline aqueous solutions containing about 20 to about 90 wt-% deuterium oxide in the aqueous portion thereof can be used to achieve a rapid lowering of the blood pressure.

Inasmuch as an isotonic saline solution can be injected into the patient without affecting the osmotic pressure of the body fluids, it is a vehicle of choice for many parenterally administered drugs. For hypertensive patients, the desired medication can be administered in deuterium-enriched saline solutions by intravenous infusion according to the extant clinical situation. Usually up to about one liter (1000 ml) of deuterium-enriched saline can be used as the vehicle for the drug or drugs. Typical unit dosage forms of deuterium-enriched aqueous saline solutions are aliquots of 100 ml, 150 ml, 250 ml, 500 ml, and 1,000 ml that contain about 0.9 weight percent of sodium chloride dissolved in water that contains about 20 to about 25 weight percent of deuterium oxide based on the total weight of the water present.

Physiological saline solutions containing deuterium also prevent cell injury, thus risk of vascular endothelial and smooth muscle cell injury that may lead to a cerebral hemorrhage can be minimized as well by the intravenous administration of such solutions.

Moreover, a life-threatening hypertensive state may occur in a female patient suffering from toxemia and/or eclampsia during pregnancy, usually during the last trimester of pregnancy. Intravenous deuterium oxide-saline solutions can be administered in such cases for a time period sufficient to ameliorate the hypertensive state.

Compositions embodying the present invention can also be used in conjunction with drugs that are usually contraindicated for hypertensive patients, especially elderly patients. For example, tricyclic antidepressant drugs such as amitriptyline hydrochloride (Elavil), imipramine hydrochloride (Tofranil), and the like, are contraindicated for hypertensive patients. However, the administration of deuterated versions of these same active ingredients can achieve the same beneficial therapeutic effect at a relatively lower dosage, thus reducing hypertension nd the accompanying risk of a stroke.

The administration of a composition containing either a deuterated food or a deuterated pharmaceutical preparation to a patient has the additional effect of enabling the deuterium to be more effectively delivered to the target tissues and time-released in the body as the deuterated compound is metabolized. Deuterated drugs are contemplated to have an increased affinity for their receptors on target tissues, such as calcium ion channels that are present on vascular smooth muscle cells. Preferred routes of administration are orally in drinking water or other ingestible liquids, orally as an aqueous methylcellulose emulsion, or intravenously as a deuterated physiological saline solution. Hypertensive patients undergoing continuous ambulatory peritoneal dialysis (CAPD) can receive deuterium from an aqueous dialysate prepared using deuterium-enriched water.

The dosage and frequency of administration to a patient exhibiting elevated blood pressure associated with hypertension varies depending upon the patient; however, the administered therapeutically effective amount is such as to elevate the deuterium concentration in the patient's body fluids by at least about 300 percent by weight, preferably to a deuterium level in the patient's body fluid in the range of about 5 percent to about 25 percent. The therapeutic dosage of deuterium, calculated as deuterium oxide, is in the range of about 12 grams (g) of $D_2O$ per day to about 675 g of $D_2O$ per day, depending on the severity of hypertension. Maintenance and prophylactic dosages of deuterium may be as low as about 10 g of $D_2O$ per day (orally) for an 80-kilogram hypertensive male patient.

A therapeutic composition of the present invention is made by distributing by dispersion or dissolution a physiologically compatible, metabolizable deuterated compound in a physiologically tolerable diluent such as water or the like. The deuterated compound is present in a concentration sufficient to supply a dosage of about 125 mg to about 8.5 g of deuterium, calculated as deuterium oxide, per kg of body weight per day to a patient upon administration.

In another preferred embodiment, a deuterated calcium channel blocker, such as deuterated verapamil or verapamil hydrochloride, is dissolved in physiological saline to produce a composition that can be administered to a patient in a conventional manner. Deuterated compounds of limited solubility in water or deuterium-enriched water can be first complexed with a solubilizing cyclodextrin, e.g., hydroxypropyl-$\beta$-cyclodextrin, or the like.

In a method of treatment aspect of the present invention, a patient with hypertension is administered a sufficient amount of a therapeutic composition, preferably a palatable liquid, containing a physiologically compatible, metabolizable deuterated compound distributed in a physiologically tolerable diluent to supply a dosage of about 12 g to about 675 g of deuterium, calculated as deuterium oxide, per day. The composition is administered for a time period sufficient to effect a decrease in the elevated blood pressure of the patient.

A further aspect of the present invention is a method for decreasing the likelihood of the onset of hypertension in a patient at risk for such a disorder. In this particular method aspect, a maintenance dose of deuterium is administered for a sustained period of time to a patient at risk but exhibiting normal-to-slightly elevated blood pressure.

This maintenance dose of deuterium can be administered to the patient daily, or at more frequent intervals, as desired. However, the amount of deuterium administered to the patient is such as to maintain a deuterium level in the patient's body fluids of at least about 0.35 percent, and preferably in the range of about 0.5 percent to about 3 percent. The foregoing deuterium levels can be maintained ordinarily by administering to the patient at least about 125 mg to about 2 g of deuterium per kg of body weight per day.

Based on animal studies, oral administration of deuterium in the form of $D_2O$ (heavy water) has been found to be effective in reducing the elevated blood pressures of hypertensive animals, as well as in preventing the onset of hypertension when administered to pre-hypertensive animals. No deleterious side effects have been noticed in animals consuming therapeutic concentrations of deuterium in their drinking water.

The present invention in one aspect contemplates the administration of deuterium via deuterated foods as an effective method for obtaining desirable anti-hypertensive effects. Similarly, it is contemplated that deuterated antihypertensive drugs can have enhanced therapeutic effects due to an enhanced affinity of the deuterated drug for their receptors on the target tissue, i.e., the calcium ion channels on vascular smooth muscle tissue.

Deuterium can also be effective in protecting calls from injury. Vascular cell injury is commonly associated with hypertension and atherosclerosis and is thought to contribute to the clinical complications associated with vascular disease such as stroke and kidney disease.

The SHR rat strain has been reported to routinely develop spontaneous hypertension, and thus is an accepted animal model for the study of hypertension. See, for example, Trippodo et al., Circulation Res. 48:309–319 (1981) and Yamori, "Physiopathology of the Various Strains of Spontaneously Hypertensive Rats" in Gemest et al., *Hypertension*, 2d. ed. (1983).

It has been found that in young (about 28 days' old) SHR rats that receive drinking water containing about 25 weight percent $D_2O$, the onset of the hypertensive elevation of blood pressure is prevented during the period of $D_2O$ administration. These rats remain at a blood pressure level comparable to that of age-matched normotensive rats during the period of $D_2O$ therapy.

The administration of drinking water containing 22.5 weight percent of $D_2O$ to hypertensive adult SHR rats (six months' old) resulted in a significant decrease of the elevated level of systolic blood pressure with time after an initial lag period of about ten days for equilibrium deuteration of body fluids.

The present invention is further illustrated by the following EXAMPLES which are not intended to limit the scope of the invention in any way.

EXAMPLE 1

Effect of $D_2O$ Administration Upon the Onset of Blood Pressure Elevation in Spontaneously Hypertensive Rats Groups of 28-day-old spontaneously hypertensive rats (SHR) purchased from Charles River Laboratories, Inc., Wilmington, Mass. 01887 (three rats/group) were placed on either standard drinking water or drinking water containing 25 weight percent $D_2O$. The systolic blood pressure of the rats was monitored by a plethysmographic method utilizing a tail cuff in which a blood pressure monitor was connected to an amplifier and a dual-channel stripchart recorder (IITC, Woodland Hills, Calif.). Age-matched Wistar-Kyoto rats (WKY) were used as normotensive controls. The systolic blood pressure was monitored two to three times per week. The results are shown in FIG. 1.

Significantly lower blood pressure was detected in young, pre-hypertensive SHR rats consuming 25 weight percent $D_2O$ in their drinking water. The control SHR rats receiving normal drinking water displayed a steady increase in systolic blood pressure throughout the 30-day time period reaching a level of 185 mm Hg at 58 days of age. The SHR rats receiving 25 weight percent $D_2O$ displayed no significant increase in systolic blood pressure, and from day 18 thereafter exhibited systolic blood pressure levels comparable to those of the normotensive WKY rat controls of about 125 mm Hg±10.

EXAMPLE 2

Figure 2:
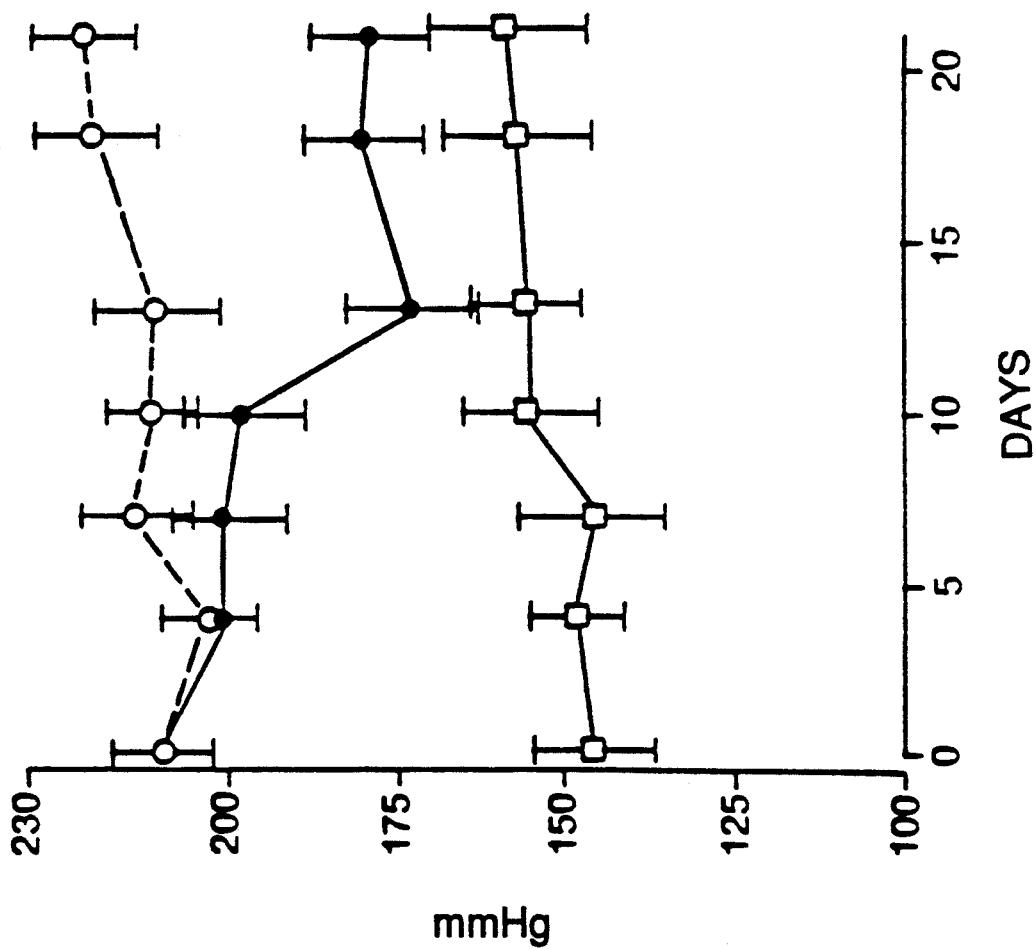
FIG. 2 is a graph illustrating the effect of deuterium oxide administration to adult hypertensive SHRs about six months of age. These adult SHRs received ad libitum either standard drinking water (O———O) or drinking water containing 22.5 percent by $D_2O$ (●———●). Control WKY rats received standard drinking water (□—□).

Effect of $D_2O$ Administration Upon the Systolic Blood Pressure Level of Hypertensive Rats Six-month-old hypertensive SHR rats having systolic blood pressure levels greater than 200 mm Hg were placed on either standard drinking water or drinking water containing 22.5 weight percent $D_2O$. Age-matched WKY rats were used as normotensive controls. The systolic blood pressure of the rats was monitored as described in EXAMPLE 1. The results are illustrated in FIG. 2.

The SHR rats receiving 22.5 weight percent $D_2O$ in their drinking water showed a significant decrease in systolic blood pressure after about 13 days of administration. It was noteworthy that this blood pressure decrease took place after the time period required to attain equilibrium deuteration of body fluids (about 10-11 days). The SHR rats receiving standard drinking water maintained elevated systolic blood pressures of about 220 mm Hg or higher. The blood pressure level in SHR rats receiving 22.5 percent $D_2O$ approached that of the normotensive WKY rats.

The foregoing description and the EXAMPLES are intended as illustrative and are not to be taken as limiting. Still other variations within the spirit and scope of this invention are possible and will readily present themselves to those skilled in the art.

I claim:

1. A method of treatment for hypertension in a patient comprising administering to said patient exhibiting an elevated blood pressure a therapeutically effective amount of deuterium oxide contained in water in an amount in the range of about 10 weight percent to about 90 weight percent based on the weight of water for a time period sufficient to effect a reduction of said blood pressure in said patient.

2. The method in accordance with claim 1, wherein said deuterium-containing composition is administered orally.

3. The method in accordance with claim 1, wherein said administration is continued so as to maintain a reduction in systolic blood pressure of at least about 10 percent.

4. The method in accordance with claim 1, wherein said administration is continued at least until an equilibrium deuteration of the patient's body fluids has been attained.

5. The method in accordance with claim 1, wherein said administration is continued for a time period of at least about 14 days.

6. The method in accordance with claim 1, wherein the deuterium oxide is contained in water in an amount of about 22.5 to about 25 percent by weight of the water.

7. The method in accordance with claim 1, wherein said deuterium-containing composition is deuterium oxide contained in physiological saline and wherein said composition is administered intravenously.

8. A method of decreasing the likelihood of the onset of hypertension in a patient at risk for hypertension which comprises administering to said patient about 12 grams to about 675 grams of deuterium oxide per day, and wherein the administration is continued daily while said patient remains at risk.

9. The method in accordance with claim 8, wherein said deuterium oxide is administered orally.

10. The method in accordance with claim 8, wherein said deuterium oxide is contained in deuterated physiological saline and is administered intravenously.

* * * * *